United States Patent [19]

Cully et al.

[11] Patent Number: 4,980,180
[45] Date of Patent: Dec. 25, 1990

[54] PROCESS FOR THE REMOVAL OF β-CYCLODEXTRIN FROM EGG YOLK OR EGG YOLK PLASMA

[75] Inventors: Jan Cully, Rosenheim; Heinz-Rüdiger Vollbrecht, Altenmarkt, both of Fed. Rep. of Germany

[73] Assignee: SKW Trostberg Aktiengesellschaft, Trostberg, Fed. Rep. of Germany

[21] Appl. No.: 491,780

[22] Filed: Mar. 12, 1990

[30] Foreign Application Priority Data

Jan. 20, 1990 [DE] Fed. Rep. of Germany ....... 4001611

[51] Int. Cl.$^5$ ................................................ A23L 1/32
[52] U.S. Cl. ........................................ 426/47; 426/614
[58] Field of Search ................. 426/7, 32, 47, 64, 614, 426/478, 495

[56] References Cited

U.S. PATENT DOCUMENTS

| | | | |
|---|---|---|---|
| 1,870,269 | 8/1932 | Tressler | 426/47 |
| 3,260,606 | 7/1966 | Azuma | 426/47 |
| 3,510,315 | 5/1970 | Hawley | 426/47 |
| 3,598,613 | 8/1971 | Hawley | 427/47 |

*Primary Examiner*—Marianne Cintins
*Attorney, Agent, or Firm*—Felfe & Lynch

[57] ABSTRACT

A process for the removal of β-cyclodextrin from egg yolk or egg yolk plasma, wherein the material to be treated is mixed and incubated with an α-amylase selected from the α-amylases formed by or derived from micro-organisms of the group *Aspergillus niger, Aspergillus oryzae, Bacillus polymyxa, Bacillus coagulans* and *Flavobacterium* or domestic hog pancreas amylase.

8 Claims, No Drawings

, 180

PROCESS FOR THE REMOVAL OF β-CYCLODEXTRIN FROM EGG YOLK OR EGG YOLK PLASMA

FIELD OF THE INVENTION

The present invention is concerned with a process for the removal of β-cyclodextrin from egg yolk or egg yolk plasma which remains behind in the egg yolk in the case of the removal of cholesterol and cholesterol esters from egg yolk with the help of β-cyclodextrin.

BACKGROUND OF THE INVENTION

It is known that increased cholesterol values in blood serum of humans represent an increased risk factor for arteriosclerosis and of coronary heart disease.

For this reason, endeavors of the foodstuff industry have the object of distinctly reducing the content of cholesterol and of cholesterol esters in fat-rich foodstuffs of animal origin, an important problem thereby being substantially to maintain the sensory and nutritional-physiological properties of the foodstuffs in the case of such a treatment.

A relatively gentle process for the removal of cholesterol derivatives is the complexing thereof with β-cyclodextrin.

Thus, for example, according to published European Patent Application No. 0,326,469, egg yolk powder, after homogenization thereof with water, is stirred for 5 hours with β-cyclodextrin at 40° C. and the complexes thereby formed are separated by centrifuging.

According to the process of as yet unpublished Federal Republic of Germany Patent Application P No. 39 28 258.9, egg yolk plasma, which has previously been separated from the LDL granula fraction by centrifuging with the help of an emulsion-breaking agents, such as water, is exclusively mixed with β-cyclodextrin. Subsequently, the so-treated egg yolk plasma, after separation thereof from the β-cyclodextrin, is again combined with the LDL granula fraction. In the case of this process, in the separation methods employed (centrifuging, filtration), it cannot be avoided that a part of the dissolved β-cyclodextrin remains behind in the egg yolk or egg yolk plasma.

Cyclodextrins (α, β, γ), which are cyclic oligosaccharides consisting of 6 to 8 glucose units, are, according to previously known investigations, toxicologically harmless. Thus, for examples, tests for acute toxicity on mice and rats have, in the case of oral administration, given no indication of a toxic effect. However, in many countries, cyclodextrins have hitherto not been permitted as "food additive".

OBJECT OF THE INVENTION

Therefore, it is an object of the present invention to provide a process for the removal of β-cyclodextrin from egg yolk and from egg yolk plasma which, without great technical expense, makes possible a substantial and selective removal of β-cyclodextrin from the treated egg yolk material.

DESCRIPTION OF THE INVENTION

Thus, according to the present invention, there is provided a process for the removal of β-cyclodextrin from egg yolk or from egg yolk plasma, wherein the material to be treated is mixed and incubated with an α-amylase selected from the α-amylases formed by or derived from micro-organisms of the group *Aspergillus niger, Aspergillus oryzae, Bacillus polymyxa, Bacillus coagulans* and *Flavobacterium* or domestic hog pancreas amylase.

We have, surprisingly, found that, in this way, a practically complete breakdown of the β-cyclodextrin in egg yolk and in egg yolk plasma can be achieved in an economically satisfactory manner. This was surprising because cyclodextrins have been described as being potent inhibitors of α- and β-amylases (see R. J. Weselake and R. D. Hill, Cereal Chem., 60, 98/1983) and are substantially resistant to most α- and β-amylases. Of a few α-amylase types, for example those from *Bacillus polymyxa, Aspergillus oryzae* or domestic hog pancreas amylase, it was admittedly known that they were able to hydrolyse cyclodextrins but with low velocities. Therefore, it was also not foreseeable that this activity would suffice in egg yolk to break down the β-cyclodextrin relatively quickly and completely.

In the case of the process according to the present invention, the starting material, consisting of egg yolk or egg yolk plasma, which, on the basis of a previous treatment with β-cyclodextrin, usually has a residual content of 0.1 to 1.0% by weight of β-cyclodextrin, is subjected to an enzymatic treatment.

For this treatment, the egg yolk or egg yolk plasma can be used in the form of a dilute aqueous solution, in which case, per kg. of egg yolk, there have been added, for example, 0.1 to 2 kg. of water in the course of the cholesterol removal. The pH value is then adjusted to the desired pH value of from 4.5 to 6.0 by the addition of an edible acid, for example citric acid. Subsequently, to the egg yolk material is added an α-amylase selected from the α-amylases formed by or derived from micro-organisms of the group *Aspergillus niger, Aspergillus oryzae, Bacillus polymyxa, Bacillus coagulans* and *Flavobacterium* or domestic hog pancreas amylase and then incubated. The necessary amount of α-amylase depends substantially upon the starting content of β-cyclodextrin in the egg yolk and is, as a rule, 10 to 500 FAU per g. of β-cyclodextrin to be removed (1 FAU=1 fungal αamylase unit breaks down 5.26 g. of starch in 1 hour under standard conditions; substrate: soluble starch, incubation time 7 to 20 minutes, temperature 37° C., pH=4.7. From a purely technical standpoint, it is also possible to work with comparatively large amounts of α-amylase but this quickly becomes uneconomical because it does not involve any better action. The incubation conditions, such as temperature and period of time, can be varied within wide limits but temperatures of from 5° to 65° C. have proved to be especially advantageous, in which case treatment times of from 2 to 50 hours are obtained.

A special advantage of the process according to the present invention is the fact that the amylases used can also be subjected for a short time to comparatively high temperature stressing without losing their enzymatic activity. Thus, the enzymes can also be added during pasteurization in which temperatures of up to 70° C. are briefly present. In this way, there is given a flexible carrying out of the process according to the present invention during the working up of the cholesterol-free egg yolk powder, which can take place before, during or after the pasteurization. In a preferred embodiment, the enzymatic breakdown of the β-cyclodextrin can also take place during storage. With the help of the process according to the present invention, a substantial removal of the β-cyclodextrin is possible in which the residual cyclodextrin contents lie below a limit of detection of <100 ppm.

The following Examples are given for the purpose of illustrating the present invention:

EXAMPLE 1

1 kg. of pretreated egg yolk with a content of β-cyclodextrin of 0.8 by weight was adjusted with 1M citric acid to a pH value of 5.5. Subsequently, 1000 FAU of the enzyme from *Aspergillus oryzae* in the form of the commercially available product Fungamyl ® of the firm Novo were added thereto. After incubation for 2 hours at 40° C., β-cyclo-dextrin was no longer detectable in the sample (detection limit: 100 ppm).

EXAMPLE 2

1 kg. of pretreated egg yolk was mixed together with 1000 FAU Fungamyl ® in the manner described in Example 1. This mixture was then pasteurised in a heat exchanger at 68° C. for 45 seconds, cooled to 5° C. in the course of 4 minutes and finally incubated for a further 8 days at 5° C. β-cyclodextrin could then no longer be detected in the treated sample (detection limit: 100 ppm).

EXAMPLE 3

1 kg. of egg yolk plasma which had been obtained from 1 kg. of egg yolk and 2 kg. of water and separation of the LDL granula fraction and which had a content of β-cyclodextrin of 0.3% by weight was treated at pH 5.5 with 1000 FAU Fungamyl ® in the manner described in Example 1. After a twofold concentration of the egg yolk plasma, the sample was pasteurized and incubated in the manner described in Example 2. β-cyclodextrin was no longer detectable in the treated sample (detection limit: 100 ppm).

EXAMPLE 4

To 1 kg. of pretreated egg yolk with a content of β-cyclodextrin of 0.8% by weight and with a pH of 6.9 were added 0.005 mol of calcium chloride and 800 FAU α-amylase (EC 3.2.1.1) from domestic hog pancreas. After incubation for 3 hours at 40° C. and subsequent storage for 24 hours at 8° C., the concentration of β-cyclodextrin in the egg yolk was 0.08% by weight.

EXAMPLE 5

1 kg. of pretreated egg yolk was mixed together with 950 FAU of an α-amylase crude preparation from *Bacillus coagulans* in the manner described in Example 4. After incubation for 2 hours at 37° C., the concentration of β-cyclodextrin in the egg yolk was 0.1% by weight.

EXAMPLE 6

1 kg. of preteated egg yolk was mixed together with 1200 FAU of a glucoamylase crude preparation from Flavobacterium sp. and incubated for 1 hour in the manner described in Example 4. The concentration of β-cyclodextrin in the egg yolk had then decreased to 0.2% by weight.

We claim:

1. The method of removing β-cyclodextrin from egg yolk or egg yolk plasma, which comprises mixing and incubating the material to be treated with an α-amylase selected from the α-amylases formed by or derived from micro-organisms of the group *Aspergillus niger, Aspergillus oryzae, Bacillus polymyxa, Bacillus coagulans* and Flavobacterium or domestic hog pancreas amylase.

2. The method of claim 1, wherein the egg yolk or egg yolk plasma is used in dilute aqueous solution.

3. The method of claim 2, wherein 0.1 to 2 kg. of water are added per kg. of egg yolk.

4. The method of 1, wherein the pH value is adjusted to a value of from 4.5 to 6.0.

5. The method of claim 1, wherein the α-amylase is added in an amount of from 10 to 500 FAU per g. of β-cyclodextrin to be removed.

6. The method of claim 1, wherein the incubation is carried out at a temperature of from 5° to 65° C.

7. The method of claim 1, wherein the enzyme treatment is carried out before, during or after a pasteurization.

8. The method of claim 1, wherein the incubation is carried out during storage.

* * * * *